United States Patent [19]

Howarth et al.

[11] 4,138,403
[45] Feb. 6, 1979

[54] AZABICYCLOHEPTANES

[75] Inventors: Thomas T. Howarth, Ewhurst; Allan G. Brown, Cranleigh; David F. Corbett, Reigate; Roger J. Ponsford, Westcott Dorking, all of England

[73] Assignee: Beecham Group Limited, England

[21] Appl. No.: 708,343

[22] Filed: Jul. 26, 1976

[30] Foreign Application Priority Data

Jul. 29, 1975 [GB] United Kingdom ............... 31640/75
Oct. 13, 1975 [GB] United Kingdom ............... 41888/75

[51] Int. Cl.² ........................................... C07D 498/04
[52] U.S. Cl. ......................... 260/307 FA; 260/239 A; 260/307 F; 424/272
[58] Field of Search ................... 260/307 FA; 424/272

[56] References Cited
PUBLICATIONS

Golding et al. — C. A. 83, 178893v (1975).
Klaus et al. — Ann. Chem. 1974, 539–60.

Primary Examiner—Raymond V. Rush
Attorney, Agent, or Firm—Jacobs & Jacobs

[57] ABSTRACT

Compounds of the formula

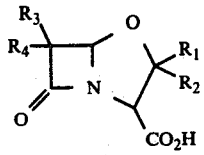

(I)

and salts and esters thereof wherein $R_1$ is hydrogen, alkyl of 1 to 4 carbon atoms, phenyl, alkenyl of 2 to 4 carbon atoms, alkynyl of 2 to 4 carbon atoms, acyl of 1 to 4 carbon atoms, a carboxylic acid group or ester thereof of 1 to 7 carbon atoms, or alkyl of 1 to 4 carbon atoms substituted by 1 or 2 halogen atoms, hydroxyl, substituted hydroxyl, amino, protected amino, substituted thio of 1 to 7 carbon atoms, substituted sulphinyl of 1 to 7 carbon atoms, substituted sulphonyl of 1 to 7 carbon atoms, or by a carboxylic acid group or ester thereof of 1 to 7 carbon atoms;

$R_2$ is hydrogen or alkyl of 1 to 4 carbon atoms, or is joined to $R_1$ to form a cycloalkyl group of 3 to 6 carbon atoms;

$R_3$ is hydrogen, chlorine or bromine; and $R_4$ is hydrogen, halogen, azido or amino; provided that when $R_4$ is azido, $R_3$ is hydrogen and $R_1$ is methyl, $R_2$ is not methyl, and that when $R_2$, $R_3$ and $R_4$ are hydrogen and $R_1$ is hydroxyethyl or an acyl derivative thereof, the compound does not have the (2R, 3S, 5R) stereochemistry; inhibit certain β-lactamate enzymes and are useful in antiseptic and disinfectant solutions.

10 Claims, No Drawings

AZABICYCLOHEPTANES

The present invention relates to compounds which are able to inhibit certain β-lactamase enzymes and are useful in antisceptic and disinfectant solutions, to processes for the preparation of these compounds, to intermediates useful in such processes and to compositions containing these compounds.

German Patent Application No. 2411856 discloses inter alia compounds of the formula (O):

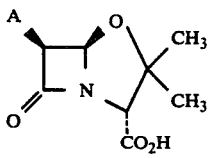

wherein A is an azido, amido or acyl substituted amido group. The compounds of the formula (O) were claimed to be useful as antibiotics but there was no suggestion that these compounds possessed any β-lactamase inhibitory properties.

We have now found a group of compounds which are structurally related to those of formula (O) and which possess β-lactamase inhibitory properties.

Accordingly in one aspect the invention provides compounds of the formula (I):

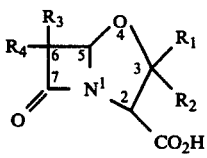

and salts and esters thereof wherein $R_1$ is a hydrogen atom or an alkyl group of 1–4 carbon atoms, a phenyl group, an alkenyl group of 2–4 carbon atoms, an alkynyl group of 2–4 carbon atoms, an acyl group of 1–4 carbon atoms, a carboxylic acid group or an ester thereof containing from 1–7 carbon atoms, or an alkyl group of 1–4 carbon atoms substituted by one or two halogen atoms, hydroxyl, substituted hydroxyl, amino or protected amino groups, substituted thiol groups containing from 1–7 carbon atoms, substituted sulphinyl or sulphonyl groups containing from 1–7 carbon atoms or by carboxylic acid groups or esters thereof containing from 1–7 carbon atoms; $R_2$ is a hydrogen atom or an alkyl group of 1–4 carbon atoms or is joined to $R_1$ to form a $C_{3-6}$ cycloalkyl group; $R_3$ is a hydrogen, chlorine or bromine atom, and $R_4$ is a hydrogen or a halogen atom or an azido or amino group with the provisos that when $R_4$ is an azido group, $R_3$ is a hydrogen atom, and $R_1$ is a methyl group, $R_2$ is not a methyl group and that when $R_2$, $R_3$ and $R_4$ are hydrogen atoms and $R_1$ is a hydroxyethyl group or an acyl derivative thereof the compound does not have the (2R, 3S, 5R) stereochemistry.

Salts of the compounds of formula (I) are preferably pharmaceutically acceptable salts. However chemically stable non-pharmaceutically acceptable salts are also useful as they may serve as intermediates in the preparation of desirable esters of the compounds of the formula (I). Salts of the compounds of formula (I) include conventional metal and ammonium salts of the carboxyl group such as the sodium, potassium, calcium, magnesium, trimethylammonium, triethylammonium and the like salts, and acid addition salts of compounds wherein $R_3$ is an amino group.

Esters of the compounds of the formula (I) are most suitably those notionally derived from alcohols of up to 16 carbon atoms. Most suitably the esters of the compounds of the formula (I) are those converted in mammalian tissues to an optionally salted acid of the formula (I) or those which may be converted by chemical means to those of the formula (I) without degradation of the bicyclic system. Such esters include those which may be converted to the parent acid or a salt thereof by hydrogenolysis or by mild acid or base catalysed hydrolysis. The term ester also includes lactones notionally derived from a hydroxyl group present in $R_1$.

Particularly suitable esters of the compounds of the formula (I) include those notionally derived from an alcohol $R^1OH$ wherein $R^1$ is a methyl benzyl, substituted benzyl, trityl, t-butyl, pivaloyloxymethyl, phthalidyl, 2,2,2-trichloroethyl, phenyl, benzoylmethyl or the like group.

When used herein the term "substituted hydroxyl group" means a $C_{1-15}$ etherified hydroxyl group, a $C_{1-14}$ acylated hydroxyl group or a $C_{1-7}$ sulphonylated hydroxyl group. Especially suitable substituted hydroxyl groups include those which may be converted by chemical methods to a free hydroxyl group under reaction conditions that do not lead to degradation of the bicyclic system. Such protected hydroxyl groups are termed herein "protected hydroxyl groups" and include etherified and acylated hydroxyl groups that may be converted to free hydroxyl groups by hydrogenolysis or by mild acid or base catalysed hydrolysis. Suitably the hydroxyl group is substituted by benzyl, p-nitrobenzyl, p-methoxybenzyl, benzhydryl, tri-$C_{1-6}$ hydrocarbyl, tri $C_{1-4}$ alkylsilyl, formyl, acetyl, dichloroacetyl, trifluoroacetyl, benzyloxycarbonyl, methyl thiomethyl or (2,2,2-trichloroethoxy)carbonyl groups or by a group

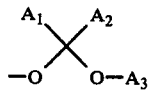

wherein $A_1$, $A_2$ and $A_3$ may all be methyl or $A_1$ may be hydrogen and $A_2COA_3$ may form a 5 to 7 membered ring or $A_3$ may be methyl and $A_1CA_2$ may form a 5 to 7 membered ring which may contain sulphur atoms.

When used herein the term "protected amino group" means an amino group sustituted by a group which may be removed by chemical means to give a free amino group under reaction conditions which do not lead to degradation of the bicyclic system.

Suitably the amino is protected by a phenyl sulphenyl, σ-nitrophenyl sulphenyl, 2,4-dinitrophenyl, formyl, trichloroacetyl, trifluoroacetyl or trityl group or by a group =CHAr (wherein Ar is a phenyl group or a phenyl group substituted by halogen atoms or nitro or $C_{1-4}$ alkoxy groups) or by a group $CO_2A_4$ wherein $A_4$ is a benzyl, p-nitrobenzyl, p-methoxybenzyl, $C_{1-8}$ alkyl (including cycloalkyl) optionally substituted by halogen atoms or $C_{1-4}$ alkoxy groups or a $C_{1-6}$ alkenyl group.

The compounds of the formula (I) wherein one or both of $R_3$ and $R_4$ are other than hydrogen atoms are useful intermediates in the synthesis of the β-lactamase inhibitory active compounds of the formula (I) wherein one or both of $R_3$ and $R_4$ are hydrogen atoms.

Suitable compounds of the formula (I) include those of the formula (II):

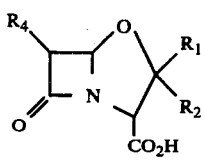

and their salts and esters wherein $R_1$, $R_2$ and $R_4$ are as defined in relation to formula (I).

Particularly suitable compounds of the formula (II) include those of the formula (III):

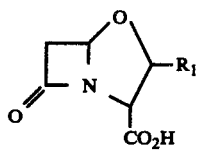

and their salts and in-vivo hydrolysable esters thereof wherein $R_1$ is as defined in relation to formula (I).

Suitably $R_1$ is a hydrogen atom or a $C_{1-4}$ alkyl group, a $C_{2-4}$ alkenyl group, a $C_{1-4}$ alkyl group substituted by halogen atoms or by hydroxy, $C_{1-7}$ acyloxy, benzyloxy, $C_{1-7}$ sulphonyloxy, phthalimido or $C_{1-6}$ alkoxy groups, or a group of the formula $CO_2R_5$ wherein $R_5$ is a hydrogen atom or a $C_{1-4}$ alkyl or benzyl group.

Preferably $R_1$ is a hydrogen atom or a $C_{1-4}$ alkyl group, a $C_{1-4}$ alkyl group substituted by a halogen atom or by a hydroxy, $C_{1-4}$ acyloxy, benzyloxy, methyl sulphonyloxy, phenylsulphonyloxy, tolysulphonyloxy, phthalimido or $C_{1-4}$ alkoxy group, or $R_1$ is a group of the formula $CO_2R_6$ wherein $R_6$ is a hydrogen atom or a benzyl group.

Preferred compounds of the formula (III) include those of the sub-formulae (IVa) and (IVb):

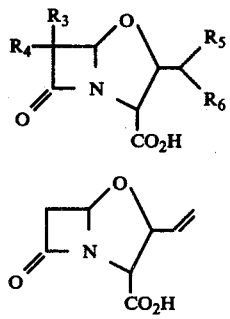

and salts and esters thereof wherein $R_3$ and $R_4$ are as defined in relation to formula (I); $R_5$ is a hydrogen atom or a $C_{1-4}$ alkyl group or a $C_{1-4}$ alkyl group substituted by a hydroxy, $C_{1-7}$ acyloxy, benzyloxy, phthalamido, methylsulphonyloxy, phenylsulphonyloxy or tolylsulphonyloxy group and $R_6$ is a hydrogen or halogen atom or a hydroxy, benzyloxy or $C_{1-7}$ acyloxy group.

Suitably $R_5$ is a hydrogen atom or a methyl group or a methyl group substituted by a phthalimidomethyl or hydroxy group.

Suitably $R_6$ is a hydrogen or halogen atom or a hydroxy group.

Suitably the relative stereochemistry at $C_2$ and $C_5$ of the compounds of the formula (I) to sub-formulae IV-(a)–(c) is the same as that found in the naturally occurring penicillins.

The present invention also provides pharmaceutical compositions which comprise a compound of the formula (I) or a salt or ester thereof together with a pharmaceutically acceptable carrier.

The compositions of this invention may be adapted for administration to human or other mammals in similar manner to known antibacterial agents. Most suitably the compositions are adapted for topical administration.

Frequently the composition of this invention will contain 100 mg–4 g of a compound of the formula (I) or a salt or hydrolysable ester thereof. Most suitably the compositions of this invention will contain 125 mg–1 g of a compound of the formula (I) or a salt thereof.

The compositions of this invention may be used in the treatment of infections caused by many gram-positive and some gram-negative bacteria, for example, on the skin.

The compounds of formula (I) are also useful for the preparation of disinfecting solutions and the like.

The present invention also provides processes for the preparation of the compounds of the invention as hereinafter described.

Method A

The present invention provides a process for the preparation of the compounds of the formula (I):

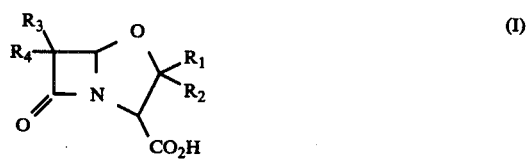

and salts thereof wherein $R_1R_2R_3$ and $R_4$ are as hereinbefore defined which process comprises the de-esterification of a compound of the formula (VI):

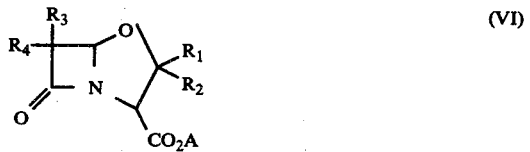

wherein the group $CO_2A$ is an ester group which may be converted to a carboxylic acid group or salt thereof under reaction conditions which do not result in degradation of the bicyclic system.

Suitably the group A is such that the ester group $CO_2A$ may be converted by mild acid or base catalyzed hydrolysis or by hydrogenolysis or photolysis to a carboxylic acid group or salt thereof. Most suitably the group A is such that the ester group $CO_2A$ may be converted by hydrogenolysis to a carboxylic acid group or a salt thereof. Preferably the group A is a methyl, benzyl, benzhydryl, trityl, substituted benzyl, substituted benzhydryl or substituted trityl group.

The benzyl group has proved to be a suitable group A which may be removed by hydrogenolysis in alkanolic solution at ambient temperature under an approximately atmospheric pressure of hydrogen using a transition metal catalyst such as palladium on charcoal.

Method B

The present invention provides a process for the preparation of esters of the compound of the formula (I):

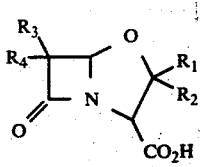
(I)

wherein $R_1$, $R_2$, $R_3$ and $R_4$ are as hereinbefore defined which process comprises the elimination of the elements of a compound of the formula HX from an ester of a compound of the formula (VII):

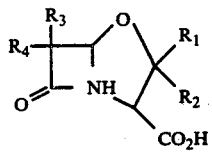
(VII)

wherein X is a group displaceable by a nucleophile.

Elimination of the elements of the compound HX from the compound of formula (VIII) normally proceeds under basic conditions. The first step in this reaction is probably the removal of the proton from the β-lactam nitrogen atom to yield an anion which then displaces the group X in an intramolecular nucleophilic diplacement reaction.

The bases used in the preceding ring-closure include conventional basic substances capable of abstracting the proton from the β-lactam nitrogen without causing degradation of the β-lactam ring. Suitable reagents include sodium hydride and lipophilic quaternary ammonium hydroxides such as N-benzyl-trimethylammonium hydroxide and mild bases such as $K_2CO_3$.

Normally the ring closure reaction is effected at a depressed temperature, for example, for −15° C. to +5° C. although temperatures outside this range may be used. We have found that temperatures of from −10° C. to 0° C. are generally satisfactory.

Suitable groups X for use in the esters of compounds of the formula (VII) include chlorine, bromine and iodine atoms and active ester groups such as O.-$SO_2.CH_3$, $O.SO_2.C_6H_4.CH_3$ and the like.

Most suitably X is one of the aforementioned halogen atoms.

We have preferred to use esters of compounds of the formula (VII) wherein X is a bromine atom.

The esters of the compounds of formula (VIII) are useful novel intermediates and as such form an important aspect of this invention.

The ring-closure of the esters of the compounds of formula (VII) is normally carried out in a solvent system such as dimethylformamide, dimethylsulphoxide, tetrahydrofuran or the like under phase transfer catalysis.

Most suitably the ester of the compound of the formula (VII) used in the ring-closure reaction is an ester of a compound of the formula (VIII):

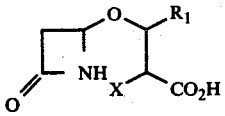
(VIII)

wherein X and $R_1$ are as defined in relation to formula (VII).

In the compounds of formula (VIII), $R_1$ is most suitably a group $R_5$ as defined in relation to formula (IV).

Most suitably the ester of the compound of the formula (VIII) is a benzyl ester or some other ester which can be cleaved by hydrogenolysis to yield the parent acid or a salt thereof.

The esters of the compound of the formula (VII) may be prepared by the reaction of a compound of the formula (IX):

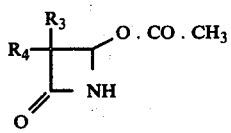
(IX)

with an ester of the compound of the formula (X):

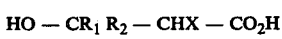
$$HO - CR_1 R_2 - CHX - CO_2H \qquad (X)$$

wherein $R_1R_2R_3R_4$ and X are as defined in relation to formula (VII).

The preceding reaction is usually performed in an inert solvent such as benzene or toluene at an elevated temperature such as 80°–100° C. in the presence of a reagent such as zinc acetate dihydrate.

We have preferred to use esters of the compounds of the formulae (VII), (VIII) and (X) which are notionally derived from an alcohol AOH wherein A is as hereinbefore defined and is most suitably a methyl or a benzyl group.

Method C

The present invention provides a process for the preparation of esters of the compound of the formula (XI):

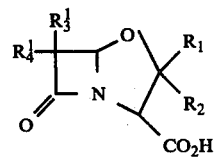
(XI)

wherein $R_1$ and $R_2$ are as defined in relation to formula (I), $R_4^1$ is a chlorine or bromine atom or an azido group and $R_3^1$ is a hydrogen chlorine or bromine atom, which process comprises the ring closing elimination of the elements of a compound HY from an ester of a compound of the formula (XII):

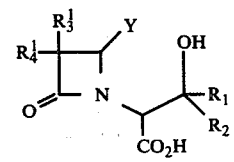
(XII)

wherein $R_1$ and $R_2$ are as defined in relation to formula (I), Y is a group displaceable by a nucleophile, $R_4^1$ is a chlorine or bromine atom or an azido group and $R_3^1$ is a chlorine, bromine or hydrogen atom.

Suitable groups Y include chlorine, bromine and groups of the formula $SR^1$, $SO.R^1$ and $SO_2R^1$ wherein $R^1$ is a lower hydrocarbon group such as a methyl or like group.

Most suitably Y is a chlorine atom.

The ring-closure is normally effected in an inert organic solvent at a non-extreme temperature, for example in methylene chloride at room temperature.

It is preferable to carry out the ring-closure in the presence of a reagent which facilitates the leaving of a $Y^\ominus$ moiety or which aids to production of an $-O^\ominus$ moiety from the alcoholic hydroxyl group. Suitable reagents include silver tetrafluoroborate and silver oxide and chemically equivalent reagents.

The compound of the formula (XII) may be prepared by the reaction of an ester of a compound of the formula (XIII):

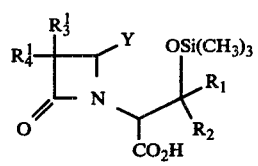

(XIII)

wherein $R_1$, $R_2$, $R_3^1$, $R_4^1$ and Y are as defined in relation to formula (XII) with water or a lower alkanol usually in the presence of an acid.

Such reactions are normally carried out at ambient temperatures.

The esters of the compounds of the formula (XIII) wherein Y is a chlorine or bromine atom may be prepared by the reaction of chlorine or bromine on a corresponding compound wherein Y is a $SR^1$ group wherein $R^1$ is a lower hydrocarbon group. Esters of the compounds of the formula (XIII) wherein Y is a $SOR^1$ or $SO_2R^1$ group may be prepared by oxidation of the corresponding compound wherein Y is an $SR^1$ group.

The esters of the compounds of the formula (XIV):

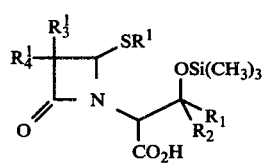

(XIV)

wherein $R^1$ is a lower hydrocarbon group and $R_1 R_2 R_3^1$ and $R_4^1$ are as defined in relation to formula (XIII) may be prepared by the reaction of a substituted ketene of the formula (XV):

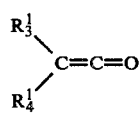

(XV)

with an ester of a compound of the formula (XVI):

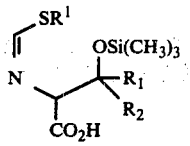

(XVI)

The substituted ketene for use in such a reaction is normally generated in situ by some conventional means such as the reaction of a tertiary amine such as triethylamine and an acid chloride or bromide of the formula (XVIIa) or (XVIIb):

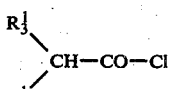

(XVIIa)

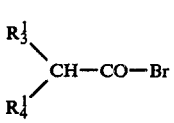

(XVIIb)

wherein $R_3^1$ and $R_4^1$ are as defined in relation to formula (XIV). The reaction of the compounds of formulae (XV) and (XVI) generally takes place in an inert organic solvent such as benzene at a non-extreme temperature such as 0°–25° C. for example, at ambient temperature.

The esters of the compounds of formula (XVI) may be prepared by the reaction of a corresponding ester of a compound of the formula (XVIII):

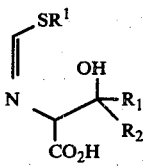

(XVIII)

with trimethylsilyl chloride, hexamethyl disilazane or the like in an inert organic solvent such as dichloromethane at a non-extreme temperature such as 0°–23° C., for example, at ambient temperature.

The esters of the compound of formula (XVIII) may be prepared by the reaction of an ester of an amino acid of the formula (XIX):

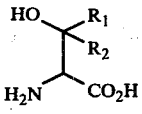

(XIX)

with a compound of the formula

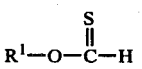

followed by alkylation with $R^1I$ or the chemical equivalent.

The first of the preceding reactions are normally carried out at depressed temperature such as $-5 - +5°$ C. in an inert solvent such as carbon tetrachloride. The alkylation reaction is generally carried out in an inert solvent such as acetone and in the presence of an acid acceptor such as $K_2CO_3$.

Method D

The present invention provides a process for the preparation of compounds of the formula (XX):

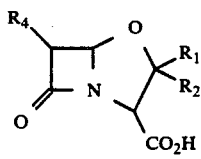
(XX)

and salts and esters thereof wherein $R_1$, $R_2$ and $R_4$ are as defined in relation to formula (I) which process comprises the reduction of a compound of the formula:

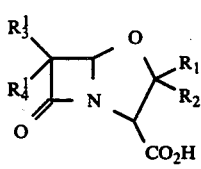
(XXI)

or a salt or ester thereof wherein $R_3^1$ is a chlorine or bromine atom and $R_4^1$ is as defined in relation to formula (XI).

Most suitably $R_3^1$ is a hydrogen or a bromine atom. Most suitably $R_4^1$ is a bromine atom or an azido group. Preferably both $R_3^1$ and $R_4^1$ are bromine atoms.

The reduction of the compound of the formula (XXI) may suitably be effected by hydrogenation using a transition metal catalyst. For example, the hydrogenation may be performed using an approximately atmospheric pressure of hydrogen in the presence of palladium on charcoal. Such reactions may take place in an organic solvent such as ethanol which, if desired, may contain a base such as sodium carbonate or the like.

The compounds of the formula (II) wherein $R_4$ is an amino group may also suitably be prepared by the reduction of a compound of the formula (XXI) by hydrogen sulphide in a suitable solvent such as methylene chloride.

It will be relalized that the compounds of the formula (I) have a number of asymmetric centres and consequently there are a number of stereo-isomeric forms of the compound of the formula(I).

The particular stereo-isomers that are formed in the preparation of compounds of the formula (I) are dependant on the preparative route that is taken to these compounds.

Thus when a compound of the formula (I) is prepared by Method B as hereinbefore described by the reaction of an azetidinone of the formula (IX):

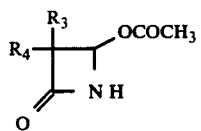
(IX)

with an ester of a compound of the formula (X):

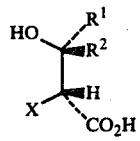
(X)

the isomeric products formed will be those wherein the substituent $R^1$ at the 3-position and ester group at the 2-position have a trans arrangement relative to one another, i.e.

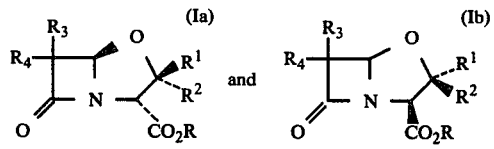

wherein $CO_2R$ is an ester group

In general there will be no preference for one of these isomers to be formed rather than the other. When the compound of the formula (X) is an optically active form then only the two stereoisomers (Ia) and (Ib) will be formed or their corresponding enantiomers but if a racemic mixture of the compound of the formula (X) is used (Ia) and (Ib) will be present with their enantiomers. When a compound of formula (I) wherein $R^2$ is hydrogen is prepared by Method C as hereinbefore described from a threo ester of an amino acid (XIX).

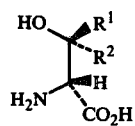
(XIX)

wherein $R_2$ is hydrogen the isomer (Ia) wherein $R^2$ is hydrogen is the chemically preferred product.

When the preparative route of Method C commences from the amino acid (XIX) wherein $R^2$ is not hydrogen then the isomeric products formed will again be (Ia) and (Ib) and in general there will be no preference for one to be formed rather than the other.

Compounds (Ia) and/or (Ib) will be formed together with their enantiomers if a racemic mixture of the amino acid (XIX) is used but on their own (or as their enantiomers) if optically active amino acid is used.

Compounds of the formula (I) wherein $R_1$ is a hydroxyl substituted $C_{1-4}$ alkyl group may be prepared from the corresponding compounds of the formula (I) wherein $R_1$ is a $C_{1-4}$ alkyl group substituted by a protected hydroxyl group by removal of the protecting group by conventional methods, such as hydrogenolysis or by mild acid or base catalysed hydrolysis. A preferred method of preparing a compound of the formula (I) wherein $R_1$ is a hydroxy substituted $C_{1-4}$ alkyl group is the hydrogenolysis of a compound of the formula (I) wherein $R_1$ is a benzyloxy substituted $C_{1-4}$ alkyl group. This hydrogenolysis reaction is suitably carried out in a suitable solvent, such as methanol or ethanol, in the presence of a transition metal catalyst, such as palladium on charcoal.

Compounds of the formula (I) wherein $R_1$ is a $C_{1-4}$ alkyl group substituted by a $C_{1-7}$ sulphonyloxy group may be prepared from the corresponding compound of the formula (I) wherein $R_1$ is a hydroxyl substituted $C_{1-4}$ alkyl group by conventional sulphonylation methods, for example by the reaction of the hydroxyl group with a sulphonyl halide such as a sulphonyl chloride, in the presence of a base, such as pyridine.

The following examples illustrate aspects of this invention:

EXAMPLE 1

Methyl 3-methoxymethyl-7-oxo-4-oxa-1-azabicyclo[3.2.0]heptane-2-carboxylate

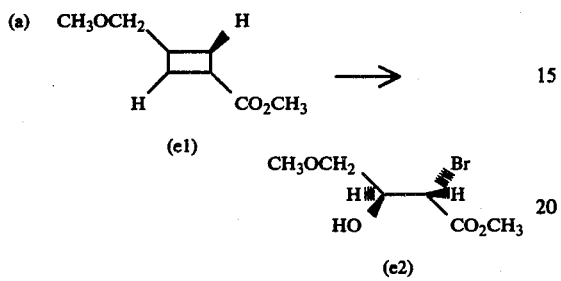

Methyl 4-methoxy-trans-crotonate (6.5 g, 50 m.mole) and N-bromoacetamide (7.6 g, 55 m.mole) were dissolved together in peroxide-free dioxane (30 ml) and water (12 ml) was added. The solution was kept at room temperature in the dark for 7 days. The resulting clear, colourless solution was diluted with ether (150 ml) and washed three times with water (50 ml portions). The solution was dried (MgSO₄) and the solvent removed under reduced pressure to yield a colourless oil (9.47 g) which was chromatographed on silica-gel (elution with ethyl acetate/petroleum ether) to give the erythro bromohydrin (e2) as a colourless oil (3.46 g, 30.5%).

$\nu_{max}$. (CHCl₃): 3500 (OH), 1740 (ester C=O) cm⁻¹.

δppm (CDCl₃): 3.42 (1H, br.s, O$\underline{H}$), 3.52 (3H, s, ether OC$\underline{H}_3$), 3.80 (2H, d, J = 3.25 Hz, OC$\underline{H}_2$), 3.93 (3H, s, ester OC$\underline{H}_3$), 4.15–4.55 (2H, complex, 2-H and 3-H).

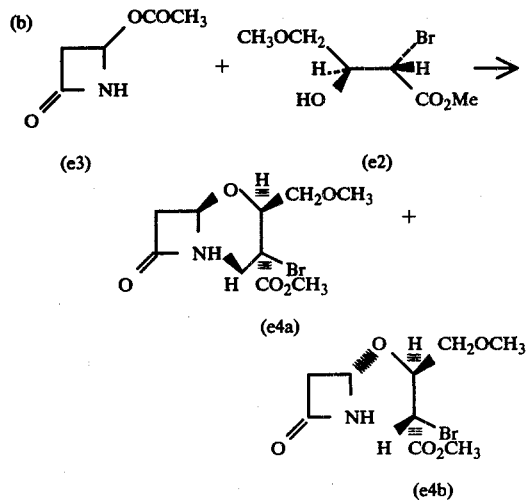

The erythro bromohydrin (e2) (800mg,5.5m mole) and 4-acetoxyazetidin-2-one (e3) (460mg, 3.5m. mole) were dissolved together in dry benzene (20 ml). Zinc acetate dihydrate (380 mg, 1.75 m.mole) was added to the solution and the mixture was stirred and refluxed with azeotropic removal of water for 24 hours. Further 4-acetoxyazetidin-2-one (200 mg) and zinc acetate dihydrate (50 mg) was then added and the reaction allowed to continue as previously described. This procedure was repeated after a further 24 hours reaction period. After a total reaction time of 72 hours, the mixture was cooled and filtered. The filtrate was diluted with ether (50 ml) and the solution was washed with saturated sodium bicarbonate solution (10 ml) and twice with water (10 ml portions). The solution was dried (MgSO₄) and the solvent removed to yield a colourless gum (720 mg). The crude procudt was chromatographed on silica-gel (15 g) using ethyl acetate/petroleum ether to yield a 1:1 mixture of the azetidinones (e4a) and (e4b) as a colourless gum (480 mg, 45%). $\nu_{max}$. (CHCl₃): 3400 and 3250 (NH), 1780 (azetidinone C=O), 1750 (ester C=O) cm⁻¹.

δ(CDCl₃): 2.7–3.4 (2H, complex, azetidinone—C$\underline{H}_2$), 3.52 (3H, s, ether OC$\underline{H}_3$), ca 3.9 (5H, s overlapped by m, ester C$\underline{H}_3$ and C$\underline{H}_2$O), 4.1–4.6 (2H, complex, 2-H and 3-H), 5.3 (1H, m, azetidinone—C$\underline{H}$), 7.2 (1H, br.s, N$\underline{H}$).

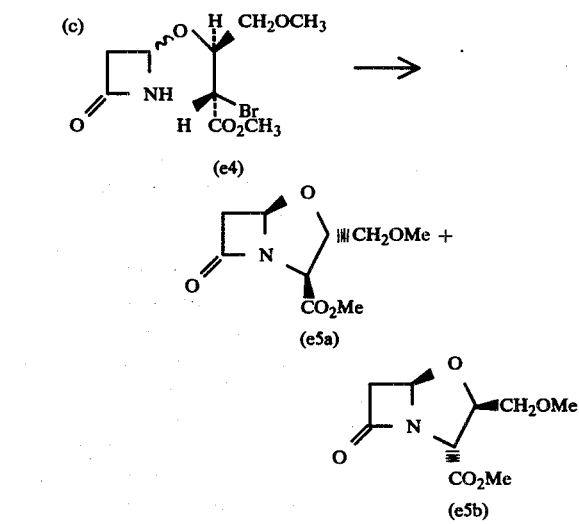

The mixture of isomeric azetidinones (e4) from (b) (260 mg, 0.9 m.mole) was dissolved in dry N,N-dimethylformamide (10 ml) and the solution was rapidly stirred at −17° (bath temperature) while 40% N-benzyltrimethylammonium hydroxide in methanol (380 mg, 0.9 m.mole) in dry N,N-dimethylformamide (1 ml) was added in one portion. The mixture was stirred at −17° for 3 minutes after addition, and then ethyl acetate (50 ml) was added. The resulting solution was washed three times with water and once with saturated brine. The solution was dried (MgSO₄) and the solvent removed to yield a pale yellow gum (150 mg) which was chromatographed on silica-gel (10 g) using ethyl acetate/petroleum ether to yield a mixture of the title compounds (e5a) and (e5b) as a colourless gum (65 mg, 34%). Repeating the above experiment with 570 mg of azetidinone mixture gave a mixture of title compounds as a colourless gum (100 mg).

The combined products (165 mg) were re-chromatographed on silica-gel (20 g) using 1:5,ethyl acetate/petroleum ether. Pure methyl (2RS,3RS,5SR)-3-methoxymethyl-7-oxo-4-oxa-1-azabicyclo[3.2.0]heptane-2-carboxylate (e5a) was obtained as a coloùrless gum (75 mg). $\nu_{max}$. (CHCl₃): 1795(azetidinone C=O) and 1750 (ester (C=O) cm⁻¹.

δ(CDCl$_3$): 2.98(1H, dd, J = 16.5 Hz, J' = 1.0 Hz, 6-H), 3.38 (1H, dd, J = 16.5 Hz, J' = 2.5 Hz, J" = 0.8 Hz, 6-H), 3.48 (3H, s, ether CH$_3$), 3.67 (2H, m, OCH$_2$), 3.92 (3H, s, ester CH$_3$), 4.05 (1H, dd, J = 5.5 Hz, J' = 0.8 Hz, 2-H), 4.80 (1H, m, 3-H), 5.50 (1H, dd, J = 2.5 Hz, J' = 1.0 Hz, 5-H). (Found M$^+$ 215.07992. C$_9$H$_{13}$NO$_5$ requires 215.07936). Pure methyl(2RS,3RS,5RS)-3-methoxymethyl-7-oxo-4-oxa-1-azabicyclo[3.2.0]heptane-2-carboxylate (e5b) was also obtained as a colourless gum (30 mg).

ν$_{max.}$ (CHCl$_3$): 1795(azetidinone C=O) and 1750 (ester C=O) cm$^{-1}$. δ(CDCl$_3$): 2.98 (1H, dd, J = 18.5 Hz, J' = 0.7 Hz, 6-H), 3.45 (1H, dd, J = 18.5 Hz, J' = 3.5 Hz, 6-H), 3.51 (3H, s, ether CH$_3$), 3.78 (2H, d, J = 3.0 Hz, OCH$_2$), 3.92 (3H, s, ester CH$_3$) 4.5–4.9 (2H, complex, 2-H and 3-H), 5.52 (1H, dd, J = 3.5 Hz, J' = 0.7 Hz, 5-H).

EXAMPLE 2

Using a method analogous to that described in Example 1 compounds of the formula (e6) were prepared.

| $X_1$ | $X_2$ | $X_3$ | Stereochemistry | Physical Data |
|---|---|---|---|---|
| CH₃ | H | CH₃ | (2RS,3SR,5SR) | νmax.(CHCl₃): 1790 (β-lactam C=O) and 1745 (ester C=O) cm⁻¹ δ (CDCl₃): 1.35 (3H, d, J 6.5 Hz, Me.CH) 2.90 (1H, dd, J 17, J' 1.5 Hz, 6β-H), 3.35 (1H, dd, J 17 J' 3.5 Hz, 6α-H), 3.52 (1H, d, J 6.5 Hz, CH.CO₂Me), 3.85 (3H, s, OMe), 4.4 – 4.8 (1H, dq, J 6.5 Hz, J' 6.5 Hz, O CH Me), 5.38 (1H, dd, J 3.5, J' 1.5 Hz, 5-H). |
| CH₃ | H | CH₃ | (2RS,3SR,5SR) | δ(CDCl₃): 1.57 (3H, d, J 6.5 Hz, CH.Me), 2.93 (1H, dd, J 17, J' 1 Hz, 6β-H), 3.40 (1H, dd, J 17, J' 3 Hz, 6α-H), 3.82 (3H, s, OMe), 4.11 (1H, d, J 6.5 Hz, CH CO₂Me), 4.22 – 4.68 (1H, dq J 6.5, J' 6.5 Hz, OCHMe) 5.37 (1H, dd, J 3, J' 1 Hz, 5-H) [Found: M⁺(mass spectrum) 186.0757. C₈H₁₂NO₄ (protonated form of molecule) requires 186.0766]. m.p. 49-51°C. |
| CH₃ | H | CH₂C₆H₅ | (2RS,3SR,5SR) (2RS,3SR,5RS) | νmax. (CHCl₃): 1790 (β-lactam C=O) and 1740 (ester C=O) cm⁻¹ δ (CDCl₃): 2.51 (3H, d, J 6.5 Hz, MeCH), 2.98 (1H, dd, J 17 J' 1Hz, 6β-H) 3.36 (1H, dd, J 17 J' 3Hz, 6α-H), 4.15 (1H, dd, J 6.5 Hz, CH CO₂), 4.67 (1H, dq J 6.5, J' 6.5 Hz, CH Me), 5.27 (2H, s, CH₂Ph), 5.4 (1H, dd, J 3, J' 1 Hz, 5-H) and 7.5 (5H, s, Ph CH₂). [Found: M⁺ + (mass spectrum) 261.1004 C₁₄H₁₅NO₄ requires 261.1001]. |
| C₂H₅ | H | CH₂C₆H₅ | Mixture of (2RS,3SR,5RS) and (2RS,3SR,5SR) | δ(CDCl₃): 1.0 (3H, t, J 7 Hz, MeCH₂), 1.45 – 1.95 (2H, m, CH₂Me), 2.75 – 3.55 (2H, m, 6-CH₂), 3.71 and 4.3 (1H, each d, J 6Hz, CH.CO₂ for major and minor isomers, respectively), 4.2 – 4.85 (1H, m, CH.CH.CH₂), 5.28 and 5.34 (2H, each s, PhCH₂ for minor and major isomers respectively), 5.4 (1H, m, 5-H) and 7.5 (5H, s, PhCH₂). [Found: M⁺ (mass spectrum) 275.1155. C₁₅H₁₇NO₄ requires 275.1157]. |
| CH₃ | CH₃ | CH₂C₆H₅ | (2RS,5SR) | νmax.(CHCl₃) 1790 (azetidinone C=O) and 1745cm⁻¹ (ester C=O); δ (CDCl₃):1.33 and 1.43 (each 3H, s, Me), 3.21 (1H, d, J 2Hz, 6-CH₂), 3.86 (1H, s, 2-H), 5.31 (2H, s, CO₂CH₂), 5.31 (1H, m, 5-H) and 7.52 (5H, s, Ph-H) [Found: M⁺ (mass spectrum) 275.1157. C₁₅H₁₇NO₄ requires 275.1157]. |
| CH₃ | CH₃ | | (2RS,5RS) | νmax.(CHCl₃) 1790 (azetidinone C=O) and 1745 (ester C=O); δ[CDCl₃):1.24 and 1.56 (each 3H, s, Me), 2.90 (1H, d, J 17 Hz 6β-H), 3.40 (1H, dd, J 17, J' 2Hz 6α-H), 4.35 (1H, s, 2-H), 5.26 (2H, s, CH₂CO₂), 5.50 (1H, d, J 2 Hz, 5-H), 7.52δ (5H, s, C₆H₅). [Found: M(mass spectrum) 275.1163. C₁₅H₁₇NO₄ requires 275.1157]. |
| CH₃ | CH₃ | CO₂Me | (2RS,5RS) | ν'max. (CHCl₃) 1790 (azetidinone C=O) and 1755 cm⁻¹ (ester C=O); δ (CDCl₃):1.32 and 1.59 (each 3H, s, Me), 2.90 (1H, d, J 17 Hz, 6β-H), 2.47 (1H, dd, J 17, J' 3 Hz, 6α-H), 3.84 (3H, s, CO₂Me), 4.34 (1H, s, 2-H) and 2.52 (1H, d, J, 3Hz, 5-H) (Found M⁺ 198, 199, 200 C₉H₁₃NO₄ requires M⁺, 199]. |
| CH₃ | CH₃ | CH₃ | (2RS,5SR) | νmax. (CHCl₃). 1790 (azetidinone C=O) and 1750 cm⁻¹ (ester C=O); δ (CDCl₃): 1.44 and 1.50 (each 3H, s, Me), 3.24 (2H, d, J 2, Hz 6-CH₂), 3.90(4H, s, CO₂Me and 2-H) and 5.37 (1H, t, J 2 Hz, 5-H) [Found: M, 200 (M⁺ + 1 ion). C₉H₁₃NO₄ requires M⁺ 199]. |
| C₂H₅ | H | CH₃ | (2RS,3SR,5RS) | νmax (CHCl₃) 1790 (β-lactam C=O) and 1745 cm⁻¹ (ester C=O); δ (CDCl₃): 1.05 (3H, m, MeCH₂), 2.1-1.6 (2H, m, CH₂Me), 2.95 (1H, d, J 17 Hz, 6β-H), 3.47 (1H, dd, J 17, J' 2.5 Hz, 6α-H), 3.88 (3H, s, MeO₂C), 4.21 (1H, d, J 7 Hz, 2-H), 4.40 (1H, dt, J 6, J' 6 Hz, 3-H) and 5.43 (1H, d, J 2.5 Hz, 5-H) [Found |

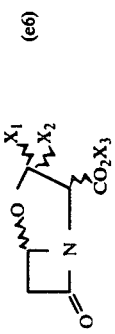

-continued

| $X_1$ | $X_2$ | $X_3$ | Stereochemistry | Physical Data |
|---|---|---|---|---|
| | | | (2RS,3SR,5SR) | M (mass spectrum) 184, 182, 171 corresponding to $M^+$—$CH_3$, $M^+$—OH, $M^+$—CO respectively]. $\nu_{max}$ (CHCl$_3$): 1790 ($\beta$-lactam C=O) and 1745 cm$^{-1}$ (ester C=O); $\delta$ (CDCl$_3$): 1.02 (3-m, MeCH$_2$), 1.5-2.0 (2H, m, CH$_2$Me), 2.98 (1H, dd, J 17, J' 1 Hz, 6$\beta$-H), 3.40 (1H, dd*, J 17, J' 2.5 Hz, 6$\alpha$-H), 3.70 (1H, d*, J 6 Hz, 2-H), 3.93 (3H, s, MeO$_2$C), 4.56 (1H, dt, J 6 Hz, 3-H) and 5.43 (1H, dd, J 2.5, J' 1 Hz, 5-H). $\nu_{max}$ (CHCl$_3$) 1795, 1750 1285, 1195 cm$^{-1}$; $\delta$(CDCl$_3$): 2.9 (1H, d) and 3.4 (1H, dd, 6-H), 3.82 (3H, s, OCH$_3$), 4.0-4.8 (3H, m, 2- and 3-H) and 5.39 (1H, m, 5-H) |
| H | H | CH$_3$ | (2RS,5RS) | m.p. 65-7° C. |
| | | | (2RS,5SR) | $\nu_{max}$ (CHCl$_3$): 1790 ($\beta$-lactam C=O) |
| CH$_2$CH$_2$Cl | H | CH$_3$ | (2RS,3SR,5SR) | and 1745 cm$^{-1}$ (ester C=O); $\delta$(CDCl$_3$): 2.07-2.38 (2H, m, CH$_2$CH$_2$Cl), 2.87 (1H, d, J 16 Hz, 6$\beta$-H), 3.38 (1H, dd, J 16, J' 2.5 Hz, 6$\alpha$-H), 3.67 (2H, t, J 7 Hz, CH$_2$Cl), 3.80 (3H, s, MeO$_2$C), 4.19 (1H, d, J 6 Hz, 2-H), 4.4-4.7 (1H, m, 3-H) and 5.36 (1H, dt, J 2.5 Hz, 5-H). |
| | | | (2RS,3RS,5RS) | $\nu$max. (CHCl$_3$): 1790 ($\beta$ lactam C=O), 1740 cm$^{-1}$ (ester C=O); $\delta$ (CDCl$_3$) : 2.08 (2H, dt, j 6.5 Hz, CH$_2$CH$_2$Cl) 2.94 (1H, dd, J 16, J' 1.5 Hz, 6$\beta$-H), 3.37 (1H, dd, J 16, J' 3Hz, 6$\alpha$-H), 3.67 (1H, d, J 6.5 Hz, 2-H), 3.68 (2H, t, J 6.5 Hz, CH$_2$Cl), 3.87 3H, s, MeO$_2$C), 4.72 (1H, dt, J 6.5, J' 6.5 Hz, 3-H) and 5.37 (1H, dd, J 3, J' 1.5 Hz, 5-H). |
| CH$_2$Br | H | CH$_3$ | (2RS,3SR,5SR) | $\nu_{max}$ (CHCl$_3$): 1795 (azetidinone C=O) and 1745 (ester C=O) cm$^{-1}$. $\delta$ppm (CDCl$_3$): 3.03 (1H, d, J = 18 Hz, J' = 1 Hz, azetidinone CHH); 3.45 (1H, dd, J = 18 Hz, J' = 2.5 Hz, azetidinone CHH); 3.68 (2H, d, J = 5 Hz, CH$_2$Br); 3.94 (3H, s, OCH$_3$); 4.06 (1H, d, J = 5.5 Hz, 2-H), 4.93 (1H, dt, J = 5.5 Hz, J' = 5 Hz, 3-H); 5.61 (1H, dd, J = 2.5 Hz, J' = 1 Hz, 5-H). |
| | | | (2RS,3RS,5RS) | $\nu_{max}$ (CHCl$_3$): 1795 (azetidinone C=O) and 1765 (ester C=O) cm$^{-1}$. $\delta$ ppm (CDCl$_3$): 3.00 (1H, d, J = 17 Hz, azetidinone CHH); 3.54 (1H, dd, J = 17 Hz, J' = 2.5 Hz, azetidinone CHH); 3.75 (2H, d, J = 4 Hz, CH$_2$Br); 3.91 (3H, s, OCH$_3$); 4.5-5.0 (2H, complex, 2-H and 3-H); 5.52 (1H, d, J = 2.5 Hz, 5-H). |
| CH$_2$CH$_2$OAc | H | Me | (2RS,3SR,5RS) | $\nu_{max}$ (CHCl$_3$) 1790 (azetidinone C=O) and 1740 cm$^{-1}$ (ester and acyl C=O); $\delta$ (CDCl$_3$) 1.9-2.4 (2H, m, CH$_2$CH$_2$O), 2.10 (3H, s, MeCO) 2.91 (1J 17 Hz, 6$\beta$-H), 3.44 (1H, dd, J 17, J' 2.5 Hz, 6$\alpha$-H), 3.85 (3H, s, MeO$_2$C), 4.1 4.7 (5H, m, 2-H, 3-H and CH$_2$O and 5.42 (1H, d, J 2.5 Hz, 5-H). |
| | | | (2RS,3RS,5RS) | $\delta$(CDCl$_3$) 1.8-2-2, (2H, m, CH$_2$CH$_2$O) 2.11 (3H, a, MeCO) 3 00 (1H, dd,) J 17, J' 1Hz, 6$\beta$-H) 3.42 (1H, dd, J 17, J' 2.5 Hz, 6$\alpha$-H 3.73 m, OCH$_2$) 4.72 (1H, dt, J 6.5, J' 6.5 Hz, 3-H) and 5.45 (1H, m, OCH$_2$) 4.72 (1H, dt, J 2.5, J' 1 Hz, 5-H). |
| CH$_2$CH$_2$OBz | H | Me | (2RS,3SR,5RS) | $\delta$ (CDCl$_3$) 2.13 (2H, dt, J 6.5 Hz, CH$_2$CH$_2$CH), 2.92 (1H, d, J 16 Hz, 6$\beta$-H), 3.37 (1H, dd, J 16, J' 3 Hz, 6$\alpha$-H), 3.68 (2H, t, J 6.5 Hz, CH$_2$CH$_2$O), 3.76 (3H, s, MeO$_2$C), 4.35 (1H, d, J 6.5 (1H, d, J 3 Hz, 5-H) and 7.41 )5H, s, CH$_2$Ph). |
| | | | (2RS,3RS,5RS) | $\delta$(CDCl$_3$) 2.00 (2H, dt, J 6.5 Hz, CH$_2$CH), 2.94 (1H, dd, J 16, J' 1Hz, 6$\beta$-H), 3.35 (1H, dd, J 16, J' 3 Hz, 6$\alpha$-H), 3.65 (2H, t, CH$_2$CH$_2$O), 3.80 (3H, s, MeO$_2$C), 3.84 (1H, d, J 6.5 Hz, 2-H), 4.52 (2H, s, PhCH$_2$), 4.73 (1H, dt, J 6.5 Hz, 3-H), 5.38 (1H, dd, J 3, J' 1 Hz, 5-H) and 7.44 (5H, s, PhCH$_2$). |
| Ph | H | Me | Mixture of | $\delta$ (CDCl$_3$) 3.10 (1H, dd, J 17, J' 1Hz, 6$\beta$-H), 3.51 (1H, dd, |

-continued (e6)

structure shown with N, O, and substituents $X_1$, $X_2$, $CO_2X_3$

| $X_1$ | $X_2$ | $X_3$ | Stereochemistry | Physical Data |
|---|---|---|---|---|
| H | H | CH$_2$Ph | (2RS,3SR,5RS) and (2RS,3SR,5SR) | $J$ 17, $J'$ 2.5 Hz, 6α-H), 3.80 (1H, d, $J$ 7 Hz, 2-H), 3.96 (3H, s, MeO$_2$C), 5.56 (1H, d, $J$ 7 Hz, 3-H), 5.65 (1H, dd, $J$ 2.5, $J'$ 1 Hz, 5-H) and 7.52 (5H, s, Ph); m/e 247 (M$^+$). Oil; $\nu_{max}$ (CHCl$_3$) 1795, 1750, 1290, 1190 cm$^{-1}$; $\delta$(CDCl$_3$) 2.82 (1H, d, $J$ = 16 Hz, β-lactam CHH), 3.30 (1H, dd, $J$ = 16 and 3Hz, β-lactam CHH), 4.11 (1H, dd, $J$ = 8 and 6 Hz), 4.33–4.70 (2H, complex), 5.18 (2H, s, CH$_2$Ph), 5.32 (1H, d, $J$ = 3 Hz, β-lactam CH), 7.37 (5H, s, Aryl-H) ppm. |
|  |  |  | (2RS,5SR) | Oil; $\nu_{max}$(CDCl$_3$) 1790, 1745, 1290, 1175 cm$^{-1}$; $\delta$ (CDCl$_3$) 2.95 (1H, dd, $J$ = 17 and 1 Hz, β-lactam CHH), 3.22 (1H, dd, $J$ = 17Hz and 2 Hz, β-lactam CHH), 3.95–4.50 (3H, complex), 5.17 (1H, m, β-lactam CH), 5.22 (2H, s, CH$_2$Ph), 7.39 (5H, s, Aryl H) ppm. |
| CH(OBz)Me | H | Me | (2RS,3RS,5RS) + (2RS,3RS,5SR) | $\delta$ ppm (CDCl$_3$): 1.15 and 1.23 (both d, $J$ 6 Hz, 3H, CH$_3$), 2.83 and 2.88 (both d, $J$ 18 Hz, 1H, β-lactam CHH), 3.18 and 3.22 (both dd, $J$ 18 Hz, $J$ 2.5 Hz, 1H, β-lactam CHH), 3.70 and 3.78 (both s, 3H, CO$_2$CH$_3$), 4.05 (d, $J$ 5Hz, 0.5 H, 2-H), 4.35–4.75 (complex, 4.5H, CHOCH$_2$Ph, 3-H, 2-H), 5.35 (m, 1H, 5-H), 7.32 (s, 5H, aromatic H). |
| —CH$_2$CH$_2$Br | H | CH$_3$ | (2RS,3SR,5RS) | (CHCl$_3$): 1790 (azetidinone C=O) and 1745 (ester C=O) cm$^{-1}$; $\delta$(CDCl$_3$): 2.15–2.55 (2H,m, CH$_2$CH$_2$Br); 2.91 (1H,d,$J$ 17 Hz, 6β-H); 3.45 (1H, dd, $J$ 16 $J'$ 3 Hz, 6α-H); 3.58 (2H, t, $J$ 6.5, CH$_2$Br); 3.85 (3H,s,MeO$_2$C); 4.22 (1H,d,$J$ 6.5Hz, 2-H); 4.4–4.75 (1H,m, 3-H) and 5.40 (1H,d,$J$ 3Hz, 5-H). |
|  |  |  | (2RS,3SR,5SR) | $\nu_{max}$(CHCl$_3$): 1790 (azetidinone C=O) and 1745 (ester C=O) cm$^{-1}$; $\delta$(CDCl$_3$): 2.22 (2H, dt, $J$ 6.5, $J'$ 6.5 Hz, CH$_2$CH$_2$Br); 3.01 (1H, dd, $J$ 17, $J'$ 1 Hz, 6β-H); 3.42 (1H, dd, $J$ 17, $J'$ 3 Hz, 6α-H); 3.60 (2H, t, $J$ 6.5 Hz, CH$_2$Br); 3.75 (1H, d, $J$ 6.5 Hz, 2-H); 3.94 (3H, s, CH$_3$O$_2$C); 4.71 (1H, dt, $J$ 6.5, $J'$ 6.5 Hz, 3-H) and 5.43 (1H, dd, $J$ 3, $J'$ 1.5 Hz, 5-H). |
| —CH$_2$CH$_2$—N(phthalimido) | H | CH$_3$ | Mixture of (2RS,3SR,5RS) and (2RS,3SR,5SR) | $\nu_{max}$ (CHCl$_3$): 1790 (azetidinone C=O), 1775 sh (phthalimido C=O), 1745 (ester C=O) and 1715 (phthalimido C=O) cm$^{-1}$; $\delta$(CDCl$_3$): 1.75–2.4 (2H, m, CH$_2$CH$_2$N); 2.75–3.5(2H, m, 6α-H and 6β-H); 3.72 and 4.22 (1H, d, $J$ 6 Hz, 2-H for major and minor isomer respectively); 4.2–3.95 (5H, m, CH$_3$O$_2$C and NCH$_2$CH$_2$); 4.4–4.8 (1H, m, 3-H); 5.4 (1H, m, 5-H) and 7.85 br (4H, aromatic-H) (Found M$^+$, 344). |

The cyclisation reaction for preparing the compound of the formula (e6) wherein $X_1 = CH_2Br$, $X_2 = H$ and $X_3 = CH_3$ was also carried out using sodium hydride (2 equivalents) in dry N,N-dimethylformamide at $-40°$ to $-25°$ over 10 minutes and gave 9% yield of the two bicyclic products.

The following conditions also effected this cyclisation but in poorer yields (2–5%).

(1) Benzyltrimethylammonium hydride (1 equivalent) in N,N-dimethylformamide at $-20°$ for 3 minutes.

(2) n-Butyl lithium (1 equivalent) in tetrahydrofuran at $-70°$ for 5 minutes.

(3) Lithium diisopropylamide (1 equivalent) in tetrahydrofuran at $-70°$ for 5 minutes.

(4) Sodium hydride (1 equivalent) in 2:1 tetrahydrofuran/dimethylsulphoxide at $-10°$ to $0°$ for 10 minutes.

(5) 1,5-Diazabicyclo[5.4.0]undec-5-enc (1 equivalent) in tetrahydrofuran at $0°$ for 40 minutes.

(6) 1N sodium hydroxide (2 equivalents) and methylene chloride with cetyltriethylammonium chloride (0.1 molar equivalent) stirred at room temperature for 1 hour.

EXAMPLE 3

Dibenzyl 7-oxo-4-oxa-1-azabicyclo[3.2.0]heptane-2,3-dicarboxylate

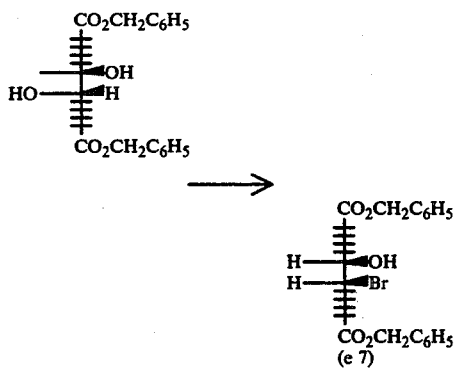

Dibenzyl (+)-tartrate (optical purity > 99%) (33 g, 0.1 mole) was dissolved in dry ether (500 ml) and the solution was stirred and ice-cooled while 2,6-lutidine (10.7 g, 0.1 mole) was added followed by trimethylchlorosilane (11.0 g, 0.1 mole). The mixture was stirred and ice-cooled with exclusion of moisture for 1 hour and then the cooling bath was removed and stirring was continued for a further 2 hours. The precipitated lutidine hydrochloride was removed by filtration and was washed with dry ether. The solvent was removed from the combined filtrate and washings to give a colourless gum (40 g). The gum was dissolved in dry ether (350 ml) and the solution was stirred while pyridine (2.0 g) was added followed by phosphorus tribromide (9.0 g). After addition was complete, the mixture was stirred at room temperature with exclusion of moisture for 3 weeks. Water (250 ml) was then added and the organic and aqueous layers were separated. The organic layer was washed three times with water (50 ml portions), dried (MgSO$_4$), and the solvent removed to yield a dark coloured gum (17 g). Chromatography of this gum on silica-gel (120 g) using ethyl acetate/petroleum ether gave bromohydrin (e7) as a colourless gum (4.1 g, 10.5%).

$[\alpha]_D^{25} = -5.9°$ (c = 1.12, CHCl$_3$). $\nu_{max.}$ (CHCl$_3$): 3500 (OH) and 1750 (ester C=O) cm$^{-1}$ $\delta$(CDCl$_3$): 3.85 (1H, br.s, OH), 4.80 (2H, br.s, 1-H and 2-H), 3.17 (2H, s, OCH$_2$), 3.20 (2H, s, OCH$_2$), 7.42 (1OH, s, ArH).

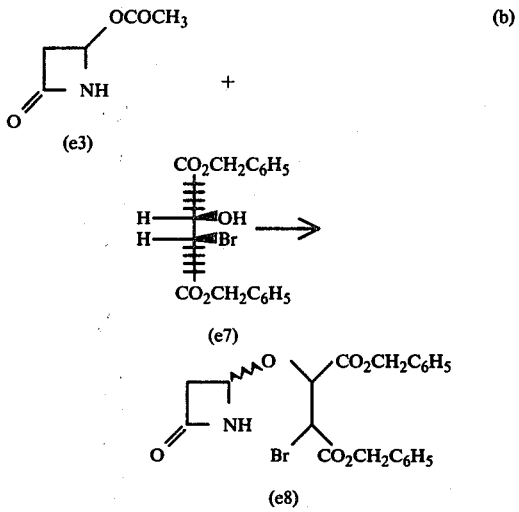

The bromohydrin (e7) (4.0 g, 10.2 m.mole) and 4-acetoxyazetidin-2-one (e3) (1.2 g) were dissolved together in dry benzene (80 ml) and zinc acetate dihydrate (880 mg) was added. The mixture was stirred and refluxed with azeotropic removal of water for 24 hours. Further 4-acetoxyazetidin-2-one (800 mg) and zinc acetate dihydrate (200 mg) were added and the reaction allowed to continue as previously described. This procedure was repeated at total reaction time 48 hours and 72 hours. After a total time of 96 hours the mixture was cooled and filtered. The filtrate was diluted with ether and washed with saturated sodium bicarbonate solution and three times with water. The solution was dried (MgSO$_4$) and the solvent removed to yield a pale yellow gum (5.5 g). Chromatography on silica-gel (40 g) using ethyl acetate/petroleum ether gave the starting bromohydrin as a colourless oil (850 mg, 21%) and a 1:1 mixture of the azetidinones (e8) as a colourless gum (3.25 g, 71%).

$[\alpha]_D^{19} = +10.2°$ (c = 0.83, CHCl$_3$). $\nu_{max.}$ (CHCl$_3$): 3450 and 3240 (NH), 1795(azetidinone C=O), 1750 (ester C=O) cm$^{-1}$; $\delta$(CDCl$_3$): 2.90 (2H, m, $\beta$-lactam CH$_2$), 4.60 (2H, m, 1-H and 2-H), 5.22 (5H, s overlapped by m, CH$_2$O, CH$_2$O and azetidinone CH), 6.85 (1H, br.s, NH), 7.42 (1OH, s, ArH).

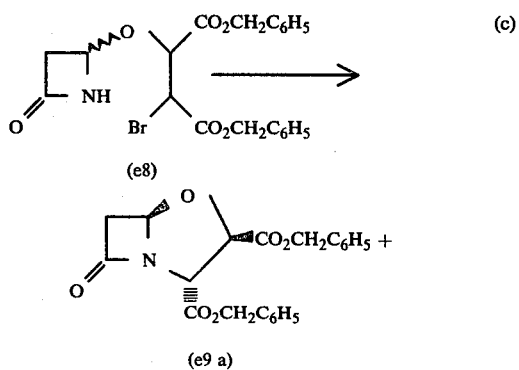

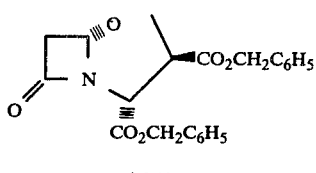

(e9 b)

The mixture of epimeric azetidinones (e8) from the foregoing experiment (250 mg, 0.54 m.mole) was dissolved in methylene chloride (5 ml) and 1.0 N sodium hydroxide solution (0.5 ml) and cetyltriethylammonium chloride (50% aqueous solution; 3 drops) was added. The mixture was vigorously stirred at room temperature and further aliquotes of 1.0 N sodium hydroxide (0.5 ml) was added at 1 hour intervals until t.l.c. indicated complete disappearance of the starting material. Ethyl acetate (50 ml) was then added and the solution was washed three times with water and once with saturated brine. The solution was dried ($MgSO_4$) and the solvent removed to yield a colourless gum (170 mg) which was chromatographed on silica-gel (15 g) using ethyl acetate/petroleum ether to yield an epimeric mixture (ca 1:1) of the title compound (e9a) and (e9b) as a colourless gum (80 mg, 39%). $[\alpha]_D^{21} = -51.8°$ (c = 0.097, $CHCl_3$). A repetition of these experiments on five-times the above scale gave a further quantity (420 mg) of the mixture (e9a) and (e9b). The combined products (500 mg) from the two preparations were repeatedly chromatographed on silica gel using 1:1 petroleum ether (b.p. 60°-80°)/dichloromethane. In this way, samples of the pure, separated epimers were obtained: Dibenzyl (2R, 3R, 5R)-7-oxo-4-oxa-1-azabicyclo-[3.2.0]heptan-2,3-Dicarboxylate (e9a) was obtained as a colourless gum, $[\alpha]_D^{21} = +6.8°$ (c = 0.12, $CHCl_3$). $\nu_{max.}$ ($CHCl_3$): 1805 (β-lactam C=O), 1750 (ester C=O) cm$^{-1}$. δ($CDCl_3$): 3.38 (br. s, 2H, 6-$CH_2$), 4.88 (d, J = 3.4 Hz, 1H, 2-CH), 5.08 (d, J = 3.4 Hz, 1H, 3-CH), 5.32 (s, 4H, $CO_2CH_2Ph$), 5.61 (d, J = 1 Hz, 5-CH), 7.43 (s, 1OH, Ar-H). Dibenzyl (2R, 3R, 5S)-7-oxo-4-oxa-1-azabicyclo-[3.2.0]heptan-2,3-dicarboxylate (e9b) was obtained as a colourless gum, $[\alpha]_D^{21} = -110.7°$ (C = 0.10, $CHCl_3$). $\nu_{max.}$ ($CHCl_3$): 1805 (β-lactam C=O), 1750 (ester C=O) cm$^{-1}$. δ($CDCl_3$): 2.8-3.4 (m, 2H, 6-$CH_2$), 4.15 (dd, J = 4.2, J' = 0.8 Hz, 1H, 2-CH), 5.22 (br.s, 5H, 3-CH, $CO_2CH_2Ph$), 5.49 br. d, J = 2Hz, 1H, 5-CH), 7.42 (s, 1OH, ArH).

EXAMPLE 4

Ethyl 6,6-dichloro-3-ethyl-7-oxo-4-oxa-1-azabicyclo[3.2.0]heptane-2-carboxylate (a) Ethyl trans-5-ethyl-2-oxazoline-4-carboxylate

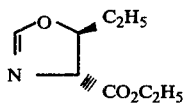

(e 10)

Sodium cyanide (1.8 g) was suspended in ethanol (70 ml) and a solution of ethyl isocyanoacetate (32.4 g) and propionaldehyde (16.7 g) in ethanol (150 ml) added dropwise with stirring at 0° C. After addition stirring was maintained for 1½ hours at 0°-5° C. and then for 1 hour at room temperature. The solvent was evaporated and carbon tetrachloride added. The solution was filtered, the solvent evaporated and the residue distilled to yield the title compound (e10) (29 g).

$\nu_{max.}$ ($CHCl_3$): 1740, 1630, 1120 cm$^{-1}$.

δ($CDCl_3$): 1.0 (t, 3H, CHCH$_2$CH$_3$), 1.3 (t, 3H, OCH$_2$CH$_3$), 1.7 (bq, 2H, CHCH$_2$), 4.0-4.8 (m, 4H, 2 × CH + CH$_2$O), 6.93 (d, J = 2Hz, 1H, C$_2$-H).

(b) Ethyl 2-amino-3-hydroxypentanoate

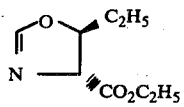

(e10)

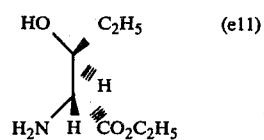

(e11)

Ethyl 5-ethyl-2-oxazoline-4-carboxylate (10.3 g), water (1.62 ml) and triethylamine (0.086 ml) were stirred at 100° C. for 3 hours. To this mixture was added 5N HCl (26 ml) and the mixture diluted to 100 ml with water, washed twice with methylene chloride and brought to pH 10 with 50% sodium hydroxide solution. The solution was extracted with methylene chloride (6 × 30 ml), dried and evaporated to yield the racemic title compound (e11) (9.4 g).

$\nu_{max.}$ ($CHCl_3$): 3340, 1725, 1220 cm$^{-1}$.

(c) Ethyl 2-thioformamido-3-hydroxypentanoate

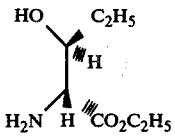

(e11)

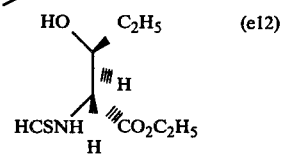

(e12)

Ethyl 2-amino-3-hydroxypentanoate (9.4 g) in carbon tetrachloride (25 ml) at 0° C. was treated with O-ethylthioformate (12 ml). The mixture was stirred for ¼ hour and H$_2$S bubbled through for ¼ hour. The mixture was stirred overnight at room temperature, evaporated and the residue chromatographed to yield the racemic title compound (e12) (8 g). Crystallised from ethyl acetate/petrol m.p. 84°-6° C.

(d) Ethyl 2-thioformamido-3-trimethylsilyloxpentanoate

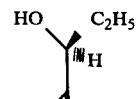

(e12)

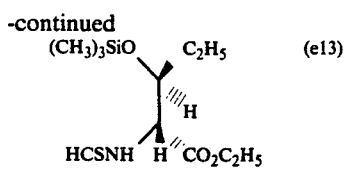

Ethyl 2-thioformamido-3-hydroxypentanoate (3.1 g) in dichloromethane (30 ml) was treated with hexamethyldisilazane (12 ml) and trimethylsilyl chloride (6 ml). The mixture was stirred overnight under nitrogen. Filtration followed by evaporation of the solvent yielded the racemic title compound (e13) (3.56 g).

$\nu_{max.}$ (CHCl$_3$): 3300, 1738, 1500, 1438, 1250, 840 cm$^{-1}$.

δ(CDCl$_3$): 0.07 (s, 9H, SiMe$_3$), 0.95 (t, 3H, CHCH$_2$C$\underline{H}_3$), 1.30 (t, 3H, OCH$_2$C$\underline{H}_3$), 1.53 (dq, 2H, CHC$\underline{H}_2$CH$_3$), 4.24 (q, 3H, OC$\underline{H}_2$CH$_3$ and C$\underline{H}$CH$_2$), 5.47 (dd, J = 9 and 1Hz, 1H, NHCS$\underline{H}$). 8.0(bs,1H,NH), 9.59(d,J6Hz,1H,HCS).

(e) Ethyl 2-(S-methylthioformimidato)-3-trimethylsilyloxypentanoate

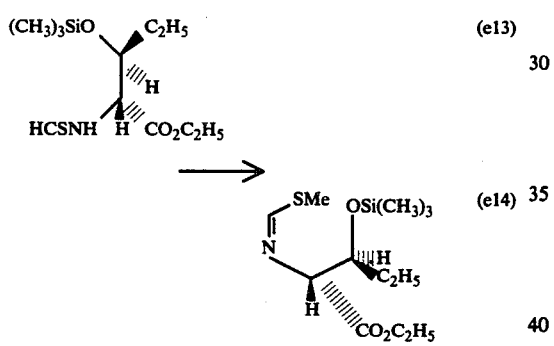

Ethyl 2-thioformamido-3-trimethylsilyloxypentanoate (3.5 g) in 25 ml acetone under nitrogen was treated with potassium carbonate (3.7 g) and methyl iodide (0.935 ml). The mixture was stirred overnight and then filtered, evaporated, dissolved in chloroform, filtered and evaporated to yield the title compound (e14) (3.66 g).

$\nu_{max.}$ (CHCl$_3$): 1730, 1595, 1250, 835 cm$^{-1}$.

δ(CDCl$_3$): 0.10 (s, 9H, SiMe$_3$), 0.94 (t, 3H, CHCH$_2$C$\underline{H}_3$), 1.28 (t, 3H, OCH$_2$C$\underline{H}_3$), ~ 1.5 (m, 2H, CHC$\underline{H}_2$, obscured), 2.42 (s, 3H, SCH$_3$), 3.8–4.4 (m, 4H, OCH$_2$ and C$\underline{H}$CH$_2$ and NCH), 8.36 (s, 1H, H-C$_1$=).

(f) Ethyl 3-hydroxy-2-(3,3-dichloro-4-methylthio-2-oxo-azetidin-1-yl)-pentanoate

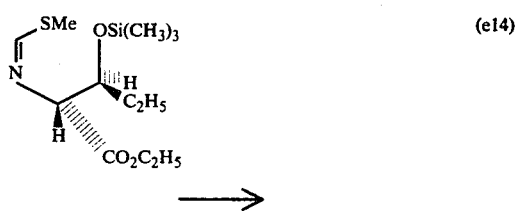

Ethyl 2-(S-methylthioformimidato)-3-trimethylsilyloxypentanoate (3 g) in benzene (150 ml) was treated under nitrogen with triethylamine (2.91 ml) and then dropwise over 6 hours with dichloroacetyl chloride (2.02 ml) in benzene (100 ml). The solution was washed with water, dried, evaporated and the residue taken up in dioxan (30 ml), containing 2.5N HCl (2.5 ml), stirred for ¼ hour and brought to pH 7 with NaHCO$_3$. The material was extracted into dichloromethane and chromatographed to yield the title compound (e15) (1.6 g).

$\nu_{max}$ (CHCl$_3$): 3400, 1785, 1740, 1270 cm$^{-1}$.

δ(CDCl$_3$): 1.04 (3H, t); 1.32 (3H, t); 1.55 (2H, q); 2.25 and 2.33 (3H, 2s); 3.13 (1H, broad s); 4.32 (4H, q); 5.15 and 5.50 (1H, 2s).

(g) Ethyl 3-hydroxy-2-(3,3,4-trichloro-2-oxoazetidin-1-yl)-pentanoate

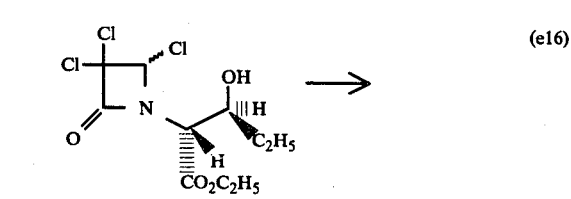

To the preceding compound (0.50 g) in carbon tetrachloride (6 ml) was added a solution of chlorine (1.1 equivalents) in carbon tetrachloride (3 ml). After 2 minutes the solution was evaporated, the residue dissolved in benzene and the resulting solution evaporated. Chromatography of the residue yielded the title compound (0.12 g).

$\nu_{max}$ (CHCl$_3$): 3270, 1790, 1735, 1260 cm$^{-1}$.

δ(CDCl$_3$): 1.07 (3H, t); 1.37 (3H, t); 1.5–1.9 (2H, m); 3.77 (1H, broad s); 4.0–4.7 (4H, m); 6.07 (1H, s).

(h) Ethyl 6,6-dichloro-3-ethyl-7-oxo-4-oxa-1-azabicyclo[3.2.0] heptane-2-carboxylate -continued

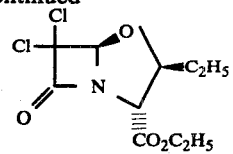
(e17)

+ C2-H major isomer), 5.39 (minor) and 5.42 (major) (2S, 1H, C5-H).

EXAMPLE 5

Using a method strictly analogous to that described in Example 4 the compounds of the formula (e18) were prepared.

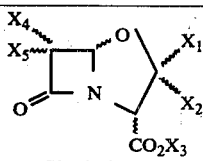
(e18)

| $X_1$ | $X_2$ | $X_3$ | $X_4$ | $X_5$ | Stereochemistry | Physical Data |
|---|---|---|---|---|---|---|
| $CH_3$ | H | $CH_3$ | Br | Br | Mixture (ratio 3:1) of (2RS,3SR,5RS) and (2RS,3SR,5SR) | $\nu_{max}$ (CHCl$_3$): 1810 (azetidinone C=O), 1750 (ester) cm$^{-1}$. δ (CDCl$_3$): 1.58 (3H, d, J=6Hz, CH—CH$_3$), 3.88 (3H, s, CO$_2$CH$_3$), 3.55 and 4.30 (1H, d, CH—CO$_2$CH$_3$, J=5Hz, two isomers in an approximate 3:1 ratio), 4.15 (1H, dq, J=5Hz, CH—CH$_3$), 5.53 (1H, s, β-lactam CH) [M$^+$ Found: 340.8882; C$_8$H$_9$NO$_4$Br$_2$ requires 340.8899]. |
| | | $C_2H_5$ | Cl | Cl | 2RS,5RS | $\nu_{max}$ (CHCl$_3$): 1805 (lactam C=O), 1740 (ester C=O) cm$^{-1}$. δ (CDCl$_3$): 1.31 (3H, t, OCH$_2$CH$_3$); 1.63 (10H, br.s, cyclohexyl H 4.24 (2H, q, OCH$_2$); 4.37 (1H, s, NCH); 5.53 (1H, s, 5-H). |
| | | | | | 2RS,5SR | $\nu_{max}$ (CHCl$_3$): 1813 (lactam C=O), 1740 (ester C=O) cm$^{-1}$. δ (CDCl$_3$): 1.32 (3H, t, OCH$_2$CH$_3$); 1.63 (10H, s, cyclohexyl H); 3.80 (1H, s, 2-H); 4.28 (2H, q, OCH$_2$); 5.27 (1H, s, 5-H). |
| $C_2H_5$ | H | $CH_3$ | Br | Br | Mixture (ratio 6:1) of (2RS,3SR,5RS) and (2RS,3SR,5SR) | $\nu_{max}$ (CHCl$_3$): 1808, 1749, 1280 cm$^{-1}$. δ(CDCl$_3$): 1.04 (3H, t, CH$_3$); 1.73 (2H, dq, CH$_2$); 3.48 (d, C2-H minor isomer); 3.80 (major) and 3.87 (minor) (3H, 2s, OCH$_3$); 4.32 (1H, dJ=4.7Hz, C2-H major isomer); 4.57 (1H, dt, J=4.7 and 6.0 Hz C3-H major isomer); 5.45 (minor) and 5.48 (major) (1H, 2s, CH—O). |
| —CH=CH$_2$ | H | $CH_3$ | Cl | Cl | (2RS,3SR,5RS) | $\lambda_{max}$ (CHCl$_3$): 1820, 1750, 1270 cm$^{-1}$. δ (CDCl$_3$): 3.90 (3H, s, OCH$_3$); 4.50 (1H, d, C2-H): 5.11 (1H, dd, C3-H): 5.3–6.1 (4H, m and s, vinyl and C5-H). m/e: 264.9908 (M$^+$) calculated for C$_9$H$_9$NO$_4$Cl$_2$: 264.9909 |
| —CH=CH$_2$ | H | $CH_3$ | Br | Br | (2RS,3SR,5RS) | Oil, $\nu_{max}$ (CHCl$_3$): 1810, 1755, 1435, 1270, 1185, 995, 855cm$^{-1}$. δ (CDCl$_3$): 3.88 (s, 3H, OCH$_3$), 4.44 (d, J=5Hz, 1H, C2-H), 5.11 (dd, J=5 and 5Hz, 1H, C3-H), 5.4–6.3 (m, vinyl-H) and 5.58 (s, C5-H, 4H in all); M/e: 353, 355, 357, (M$^+$). Found: 352.8906. Calc. C$_9$H$_9$NO$_4$Br$_2$: 352.8899. |
| $C_2H_5$ | H | $CH_3$ | $N_3$ | H | (2RS,3SR,5RS,6RS) | $\nu_{max}$ (CHCl$_3$): 2080, 1790, 1747, 1280 cm$^{-1}$. δ (CDCl$_3$): 1.00 (t, 3H, CH$_2$CH$_3$), 1.73 (dq, 2H, CH$_2$CH$_3$), 3.78 (s, 3H, OCH$_3$), 4.1–4.5 (m, 2H, C$_3$-H + C$_2$-H), 4.38 (s, 1H, C$_6$-H), 5.22 (s, 1H, C$_5$-H). δ (C$_6$D$_6$): 0.68 (t, 3H, CH$_2$CH$_3$), 1.1–1.5 (m, 2H, CH$_2$CH$_3$), 3.16 (s, 3H, OCH$_3$), 3.77 (s, 1H, C$_6$-H), 3.9–42 (m, 2H, C$_2$-H + C$_3$-H), 4.79 (s, 1H, C$_5$-H). m/e: 212 (M$^+$ −28), 185 (M$^+$ −55), 181 (M$^+$ —COOMe), 98. |
| | | | | | (2RS,3SR,5SR,6SR) | $\nu_{max}$ (CHCl$_3$): 2090, 1795, 1742, 1290, 1170 cm$^{-1}$. δ (CDCl$_3$): 1.00 (t, 3H, CH$_2$CH$_3$), 1.68 (dq, 2H, CH$_2$CH$_3$), 3.63 (dJ=5Hz, 1H, C$_2$-H), 3.83 (s, 3H, OCH$_3$), 4.3–4.5 (m, 1H, C$_3$-H), 4.50 (s, 1H, 5.19 (s, 1H, C$_5$-H). δ (C$_6$D$_6$): 0.55 (t, 3H, CH$_2$CH$_3$), 0.7–1.3 (m, 2H, CH$_2$CH$_3$), 3.02 (d, J=5, 1H, C$_2$-H), 3.26 (s, 3H, OCH$_3$), 3.77 (s, 1H, C$_6$-H), 3.9–4.2 (m, 1H, C$_3$-H), 4.51 (s, 1H, C$_5$-H). m/e: 241 (M$^+$ +1), 185, 98. |
| | | | | | (2RS,3SR,5RS,6SR) + (2RS,3SR,5SR,6RS) | $\nu_{max}$ (CHCl$_3$): 2100, 1795, 1742, 1265 cm$^{-1}$. δ (CDCl$_3$) 1.03 (t, 3H, CH$_2$CH$_3$), 1.82 (dq, 2H, CH$_2$CH$_3$), 3.79 (s, 3H, OCH$_3$), 4.1–4.5 (m, 2H, C$_2$-H + C$_3$-H), 4.50 (d J=3Hz, 1H, C$_6$-H), 5.23 (d J=3Hz, C$_6$-H minor component), 5.38 (d J=3Hz, C$_6$-H major component). δ (C$_6$D$_6$): 0.77 (t, 3H, CH$_2$CH$_3$), 1.1–1.7 (m, 2H, CH$_2$CH$_3$), 3.22 (s, 3H, OCH$_3$), 3.60 (d J=Hz, 1H, C$_6$-H), 3.9–4.2 (m, 2H, C$_2$-H + C$_3$-H), 4.74 (d J=3Hz, 1H, C$_5$. m/e: 211 (M$^+$ −29), 185, 98. |

All of the material produced in (g) was dissolved in methylene chloride (3 ml). To this solution was added AgBF$_4$ (0.074 g) and Ag$_2$O (0.44g). After stirring for ½ hour the suspension was filtered and the filtrate washed with NaHCO$_3$ and water, dried and evaporated. Chromatography of the residue yielded the title compound (e17) (0.025 g), which was a mixture of the compound with the (2RS, 3SR, 5RS) stereochemistry and also the compound (2RS, 3SR, 5SR) stereochemistry in the ratio of 10:1.

M$^+$ = 281.0222 (C$_{10}$H$_{13}$Cl$_2$NO$_4$ requires 281.0221)
$\nu_{max}$ (CHCl$_3$): 1812, 1740, 1185 cm$^{-1}$.
δ(CDCl$_3$): 1.03 (t, 3H, CH$_2$CH$_3$), 1.31 (t, 3H, OCH$_2$CH$_3$), 1.77 (dq, 2H, CH$_2$CH$_3$), 3.59 (d, J = 8Hz, C2-H minor isomer), 4.0–4.7 (m, 4H, OCH$_2$Me + C3-H The 6-azido compound and 6-dibromo compound were prepared by the substitution of azidoacetyl chloride and dibromoacetyl chloride respectively for the dichloroacetyl chloride in step (f).

EXAMPLE 6

Methyl 3-methyl-7-oxo-4-oxa-1-azabicyclo [3.2.0] heptane-2-carboxylate

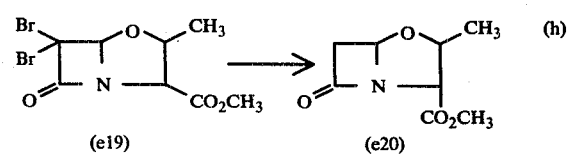
(h)

The bicycloheptane (e19) (10 mg) which had predominantly the (2RS,3SR,5RS) stereochemistry was dissolved in a mixture of ethanol (1 ml) and ethyl acetate (1 ml) and hydrogenated at normal temperature and pressure using 5% palladium on calcium carbonate as catalyst. After one hour the solution was filtered and the crude methyl 3-methyl-7-oxo-1-aza-4-oxabicyclo[3.2.0]heptane-2-carboxylate (e20) (2RS,3SR,5RS) isomer so obtained was found to be identical to the product obtained in Example 2.

The (2RS,3SR,5RS) 3-ethyl analogue of the compound of the formula (e20) was prepared by a strictly analogous method except that the reaction was carried out in the presence of a solution of sodium bicarbonate in water.

EXAMPLE 7

Ethyl 6-chloro-3-ethyl-7-oxo-4-oxa-1-azabicyclo[3.2.0]heptane-2-carboxylate

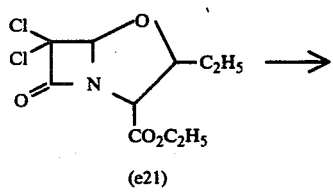

(e21)

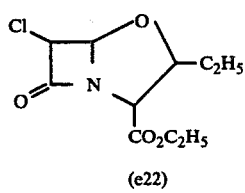

(e22)

Ethyl 6,6-dichloro-3-ethyl-7-oxo-1-aza-4-oxabicyclo[3.2.0]heptane-2-carboxylate (e21) (25mg, 0.089 m.mole) in EtOH/H$_2$O containing 2 equivalents of NaHCO$_3$ was hydrogenated over Pd/CaCO$_3$ for 45 minutes, extracted into ethyl acetate, dried and evaporated under reduced pressure. Chromatography yielded the title compound (e22) (9 mg, 41%) M$^+$ 247.0612 C$_{10}$H$_{14}$ClNO$_4$ requires 247.0611

$v_{max.}$ (CHCl$_3$): 1800 (azetidinone (C=O), 1743 (ester C=O) cm$^{-1}$.

$\delta$(CDCl$_3$): 1.03 (3H, t, CHCH$_2$CH$_3$), 1.36 (3H, t, OCH$_2$CH$_3$), 1.5–1.9 (2H, m, CHCH$_2$), 4.1–4.8 (5H, m, OCH$_2$, C2-H, C3-H, C6-H), 5.40 (1H, s, C5-H).

EXAMPLE 8

3-Methyl-7-oxo-4-oxa-1-azabicyclo[3.2.0]heptane-2-carboxylic acid

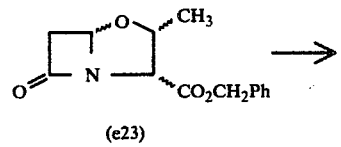

(e23)

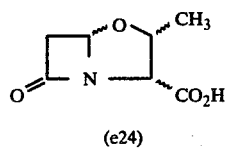

(e24)

A solution of the bicyloheptane (e23) obtained from Example 2 in ethyl alcohol was hydrogenated in the presence of palladium on charcoal for 2 hours. The material obtained after filtration and evaporation of the solution contained the acid (e24): $v_{max.}$ (CHCl$_3$): 1790 (azetidinone C=O) and 1725 cm$^{-1}$ (carboxylic C=O).

EXAMPLE 9

Sodium 3,3-dimethyl-7-oxo-4-oxa-1-azabicyclo[3.2.0]heptane-2-carboxylate

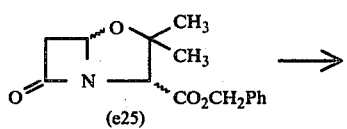

(e25)

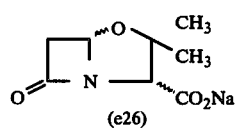

(e26)

The benzyl ester (e25) (0.023 g, 0.084 m.mole) obtained from Example 2 was dissolved in ethanol (5 ml) containing 10% Pd-C catalyst (0.008 g) and NaHCO$_3$ (0.007 g). The solution was hydrogenated for 15 minutes, filtered and washed well with water. Removal of the solvents under reduced pressure gave the title compound (e26).

$v_{max.}$ (KBr) 1760 (azetidinone C=O) and 1595 cm$^{-1}$ (carboxylate C=O)

$\delta$(D$_2$O): 1.37 and 1.57 each (3H, s, Me), 2.88 (1H, dd, J 17, J' = 0.5 Hz, 6$\beta$-H), 3.42 (1H, dd, J 17, J'=2 Hz, 6$\alpha$-H), 4.13 (1H, s, 2-H), 5.48 (1H, d, J=2 Hz, 5-H).

EXAMPLE 10

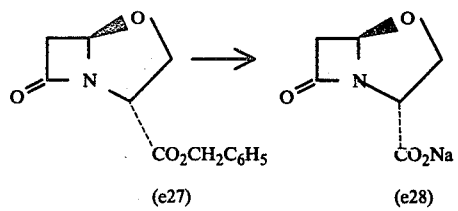

(e27)           (e28)

(a) A solution of the benzyl ester (e27) (1.38g) obtained from Example 2, in ethanol (40 ml), containing solid sodium bicarbonate (470 mg, 1 equiv.), was treated with water until an homogeneous solution was obtained. The solution was then hydrogenated (1 atm., 20°) over 10% palladium on charcoal (1.0 g), diluted with water and filtered through celite. The ethanol was evaporated in vacuo and the resulting aqueous solution washed with ether. Freeze-drying afforded the sodium salt (e28) as a solid (ca.1 g). $v_{max}$(KBr disc) 1770 ($\beta$-lactam), 1600 (CO$_2^-$), 1195, 1050 cm$^{-1}$.

(b) The same compound can be obtained by hydrolysis of the corresponding methyl ester, dissolved in aqueous tetrahydrofuran at 20° using N-sodium hydroxide to maintain the pH at 9.2 (pH-stat control). After 1.5 hrs. hydrolysis is complete and the title compound is obtained by ether extractions and freeze-drying of the aqueous solution after adjustment of the pH to 7.1.

EXAMPLE 11

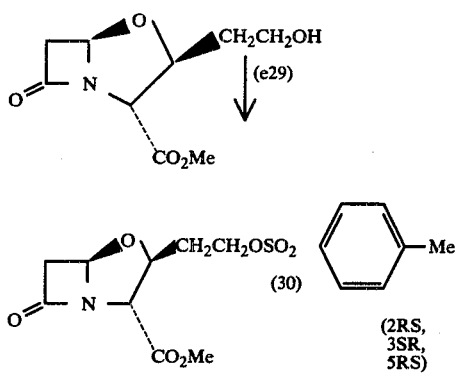

The hydroxyethyl compound (e29) (0.137 g, 0.64 mmole) was dissolved in methylene chloride (2 ml) and treated with a solution of pyridine (0.055 g) in methylene chloride (1 ml), and then with p-toluene sulphonyl chloride (0.137 g) at 0°–5°. After 1 hr. at 0° and 18 hrs. at 20° more sulphonyl chloride (0.05 g) and pyridine (0.055 g) were added. After a further 6 hours, the mixture was diluted with ethlacetate, washed with sodium bicarbonate solution, and water, dried and evaporated. Chromatography if the residue on silica gel eluting with petrolethyl acetate provided the title compound (e30) as a clear colourless gum (53% yield)..

Oil; $\nu_{max}$ (CHCl$_3$): 1790, 1750, 1600, 1360, 1180, 1010 cm$^{-1}$;

δ(CDCl$_3$): 2.17 (dt, 2H, C$\underline{H}_2$), 2.51 (s, 3H, Ar-C$\underline{H}_3$), 2.86 (d, J = 17 Hz, 1H, C6-trans-H), 3.40 (dd, J = 17 and 3 Hz, 1H, C6-cis-H), 3.88 (s, 3H, OC$\underline{H}_3$), 4.1–4.7 (m, 4H, C$\underline{H}_2$O + C$\underline{H}$), 5.4 (d, J = 3 Hz, 1H, C5-H) and 7.49, 8.01 (dd, 4H, Ar-H).

EXAMPLE 12

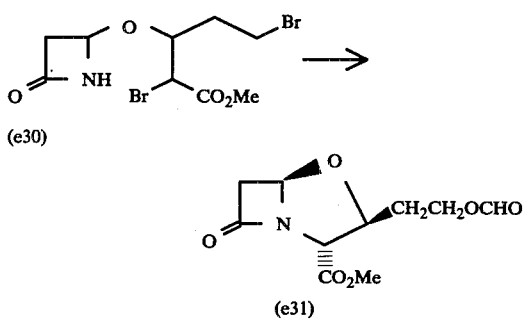

The azetidinone (e30) (0.3 g 0.84 mml) was treated with K$_2$CO$_3$ (0.264 g 1.9 mml) and HCOONa (0.114 g, 1.68 mml) in dry DMF (6 ml). After 40 hour work-up and chromatography afforded the 2-formyloxyethyl compound (e31) as a separable mixture of the (2RS, 3SR, 5RS) and (2RS, 3SR, 5SR) isomers (total 20% yield)

(2SR, 3SR, 5RS) $\nu_{max}$ (CHCl$_3$) 1790 (azetidinone C=O) and 1730–1740 br cm$^{-1}$ (ester and acyl C=O);

δ (CDCl$_3$): 1.95–2.35 (2H, m, CH$_2$CH), 2.93 (1H, d, J 17 Hz, 6β-H), 3.42 (1H, dd, J 17, J', 2.5 Hz, 6α-H), 3.84 (3H, s, MeO$_2$C), 4.2–4.8 (4H, m, 2-H, 3-H and CH$_2$OCO), 5.40 (1H, d, J 2.5 Hz, 5-H), and 8.18 (1H, s, OCHO).

(2RS, 3SR, 5SR) $\nu_{max}$ (CHCl$_3$) 1790 (azetidinone C=O), 1740 (ester C=O) and 1725 cm$^{-1}$, (formyl C=O); δ(CDCl$_3$): 1.85–2.2 (2H, m, C$\underline{H}_2$), 2.97 (1H, dd, J 6.5 Hz, 2-H), 4.36 (2H, dt, J 6.5 Hz, C$\underline{H}_2$CH) 4.67 (1H, dt, J 6.5, J' 6.5 Hz, 3-H), 5.40 (1H, d, J 2.5, J' 1Hz, 5-H), 8.17 (1H, s, OCHO).

EXAMPLE 13

Methyl (2RS, 3RS, 5 RS)-AND (2RS, 3RS, 5SR)-3-(1-hydroxy-ethyl)-7-oxo-4-oxa-1-azabicyclo [3.2.0]heptane-2-carboxylate

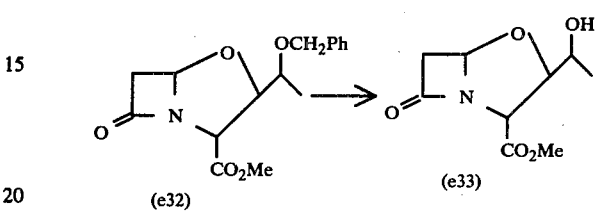

Methyl 3-(1-benzyloxyethyl)-7-oxo-4-oxa-1-azabicyclo[3.2.0]heptane-2-carboxylate (e32) (90 mg) obtained from Example 2 and 10% palladium-on-charcoal (90 mg) in ethanol (2 mls) were shaken under one atmosphere of hydrogen at room temperature for 2 hours. The catalyst was removed by filtration and was washed well with ethyl acetate. Evaporation of the solvent from the combined filtrate and washings, gave methyl 3-(1-hydroxyethyl)-7-oxo-4-oxa-1-azabicyclo [3.2.0]heptane-2-carboxylate as a colourless gum (45 mg).

$\nu_{max}$ (CHCL$_3$): 3370 (OH), 1785 (β-lactam C=O), 1740 (ester C=O) cm$^{-1}$. δ(CDCl$_3$): 1.20 and 1.25 (both d, J 17 Hz, 1H, 6-CH$\underline{H}$), 3.40 (br.d, J 17 Hz, 1H, 6-C$\underline{H}$H), 3.90 and 3.98 (both s, 3H, CO$_2$CH$_3$), 4.0–4.85 (complex, 3H, 2-CH, 3-CH, C$\underline{H}$OH), 5.50 (d, J 2Hz, 5-CH).

In a similar fashion to the above the following were prepared from the corresponding benzyl ethers.

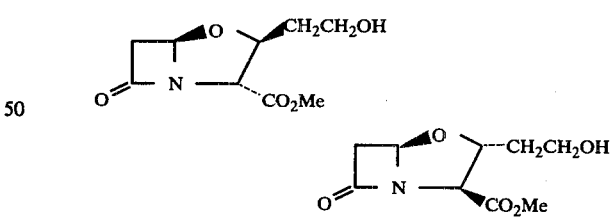

(2RS, 3SR, 5RS) δ (CDCl$_3$) 1.95 br (1H, OH, disappears with D$_2$O), 2.10 (2H, dt, J 6.5 Hz, C$\underline{H}_2$CH), 2.95 1H, d, J 17 Hz, 6β-H), 3.43 (1H J' 3 Hz, 6α-H) 3.73–4.0 (5H, m, CH$_2$C$\underline{H}_2$O and MeO$_2$C), 4.32 (1H, d, J 6.5 Hz, 2-H), 4.43–4.75 (1H, m, 3-H) and 5.39 (1H, d, J 3 Hz, 5-H); m/e 215 (M$^+$).

(2RS, 3SR, 5SR) δ (CDCl$_3$): 1.92 (2H, dt, J 6.5 Hz, CH$_2$CH), 2.18 br. (1H, OH, disappears with D$_2$O), 2.98 (1H, dd, J 17, J' 1Hz, 6β-H), 3.40 (1H, dd, J 17, J' 3Hz, 6α-H), 3.75–3.95 (6H, m, 2-H, CH$_2$C$\underline{H}_2$O and MeO$_2$C), 4.5–4.8 (1H, m, 3-H) and 5.45 (1H, m, 5-H).

EXAMPLE 14 method described in Belgian Patent No. 827,926 and the results are shown in Table 1.

Table 1

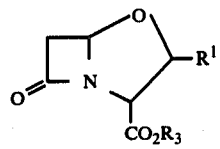
(e36)

% Inhibition of - lactamases at 40 μg/ml or $I_{50}$ values (μg/ml in parentheses)

| $R_1$ | $R_3$ | Stereo-chemistry | Citro-bac. | Ps. aerug. | Proteus C889 | E.Coli JT4 | Kleb. ε 70 | Ps. dalgl. | Staph. Russell |
|---|---|---|---|---|---|---|---|---|---|
| $CO_2CH_2Ph$ | $CO_2CH_2Ph$ | (2R,3R,5R) | 2 | 9 | 23 | 65 | 56 | 26 | 0 |
| $CH_2Br$ | $CO_2CH_3$ | (2RS,3RS,5RS) | (10.3) | 8 | 42 | 42 | 4 | 17 | 12 |
| H | Na | (2RS,5RS) | 0 | 14 | — | 28 | 78 | 0 | 33 |
| $CH_2CH_2O\text{-}C_6H_4\text{-}Me\text{-}SO_2$ | Me | (2RS,3SR,5RS) | 5 | 11 | — | 33 | 0 | 11 | 4 |
| $CH_2CH_2OH$ | Me | (2RS,3SR,5RS) | 2 | 10 | 29 | 15 | 14 | 0 | 10 |

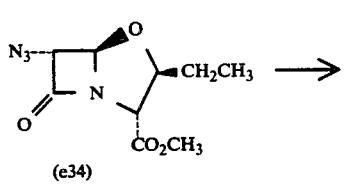
(e34)

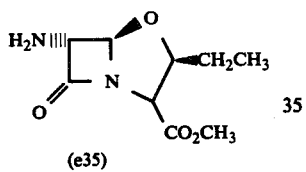
(e35)

A solution of methyl (2RS, 3SR, 5RS, 6RS,) 6-azido-3-ethyl-7-oxo-4-oxa-1-azabicyclo [3.2.0] heptane-2-carboxylate (e34) (0.019g. 0.079 m mole) obtained from Example 5 in 3 ml. $CH_2Cl_2$ was treated with triethylamine (0.022 ml., 0.158 m mole) in 1 ml $CH_2Cl_2$ and cooled in ice/salt to $-5°-0°$ C. Hydrogen sulphide was bubbled through the stirred solution for 15 mins. and stirring continued for a further 15 mins. before evaporating. $CH_2Cl_2$ was added and evaporated twice. $\nu_{max}$ ($CH_2Cl_2$): 1781, 1740 cm$^{-1}$.

The title compound was characterised by phenoxyacetylation. The above crude amino compound in 3 ml. ice cooled $CH_2Cl_2$ was treated with pyridine (0.019 ml, 0.237 m mole) in 1 ml $CH_2Cl_2$ and then dropwise with phenoxyacetyl chloride (0.0136 g, 0.080 m mole) in 1 ml $CH_2Cl_2$. The solution was stirred 15 mins. at 0°–5° C., washed with pH 7 buffer, dried and evaporated. Chromatography provided the required (2RS, 3SR, 5RS, 6RS) phenoxyacetamido derivative in 18% overall yield.

$\nu_{max}$ (CHCl$_3$): 3380, 1792, 1747, 1690, 1598, 1512, 1490, 1210cm$^{-1}$.

δ (CDCl$_3$): 0.99 (t, 3H, CH$_2$C$\underline{H}_3$), 1.73 (dg, 2H, C$\underline{H}_2$CH$_3$), 3.76 (s, 3H, OCH$_3$), 4.1–4.5 (m, 2H, C$_2$-H + C$_3$-H),, 4.51 (s, 2H CH$_2$CO), 4.99 (d J = 9 Hz, J = 0, 1H, C$_6$-H), 5.26 (s, 1H, C$_5$-H), 6.8-7.4 (m, 6H, Ph + NH). m/e 348.13221 (M$^+$): C$_{17}$H$_{20}$N$_2$O$_6$ requires 348.13212.

The β-lactamase inhibiting activity of certain compounds of the formula (e36) was determined by the

We claim:

1. A compound of the formula

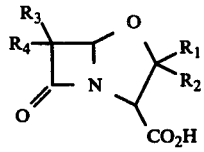

or a pharmaceutically acceptable salt thereof wherein
$R_1$ is hydrogen, alkyl of 1 to 4 carbon atoms, phenyl, acyl of 1 to 4 carbon atoms, a carboxylic acid group or benzyl ester thereof, or alkyl of 1 to 4 carbon atoms substituted by 1 or 2 halogen atoms;
$R_2$ is hydrogen;
$R_3$ is hydrogen; and
$R_4$ is hydrogen.

2. A compound according to claim 1 in the form of a pharmaceutically acceptable salt.

3. A compound according to claim 1 having the same relative stereochemistry at $C_2$ and $C_5$ as the naturally occurring penicillins.

4. The compound according to claim 1 which is 3-methyl-7-oxo-4-oxa-1-azabicyclo[3.2.0]heptane-2-carboxylic acid.

5. The compound according to claim 1 which is sodium 3,3-dimethyl-7-oxo-4-oxa-1-azabicyclo[3.2.0]heptane-2-carboxylate.

6. The compound according to claim 1 of the formula

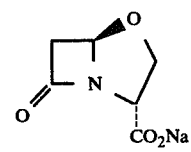

7. The compound according to claim 1 of the formula

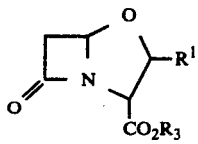

wherein $R_1$ is hydrogen, $R_3$ is sodium and the stereo configuration of the compound is (2RS, 5RS).

8. A compound according to claim 1 wherein $R_1$ and $R_2$ are each hydrogen.

9. A compound according to claim 8 in the form of a pharmaceutically acceptable salt selected from the group consisting of the sodium, potassium, calcium, magnesium, trimethylammonium and triethylammonium salts.

10. Methyl 3-bromomethyl-7-oxo-4-oxa-1-azabicyclo[3.2.0]heptane-2-carboxylate.